United States Patent [19]

Babler

[11] 4,314,071

[45] Feb. 2, 1982

[54] METHOD OF PREPARING MONOESTERS

[76] Inventor: James H. Babler, 125 Callan Ave., Evanston, Ill. 60202

[21] Appl. No.: 148,922

[22] Filed: May 12, 1980

Related U.S. Application Data

[63] Continuation-in-part of Ser. No. 954,363, Oct. 25, 1978, abandoned.

[51] Int. Cl.$^3$ .............................................. C07C 69/75
[52] U.S. Cl. .................... 560/127; 560/177; 560/204; 560/261; 560/263; 562/595; 560/248; 560/231
[58] Field of Search ............... 560/204, 203, 248, 231, 560/127

[56] References Cited

U.S. PATENT DOCUMENTS 4,082,788  4/1978  Mims ................................... 560/204

FOREIGN PATENT DOCUMENTS 2015709  10/1972  Fed. Rep. of Germany ........ 560/71
2404359   8/1974  Fed. Rep. of Germany ...... 560/204

*Primary Examiner*—Paul J. Killos
*Attorney, Agent, or Firm*—Merriam, Marshall & Bicknell

[57] ABSTRACT

Monoesters of symmetrical dicarboxylic acids and symmetrical diols are prepared in high yield by reacting a diacid or a diol with a monohydric alcohol or monocarboxylic acid, respectively, in an aqueous solution. The resultant monoester is removed from the aqueous solution immediately after its formation by continuous extraction with a nonpolar solvent.

10 Claims, No Drawings

METHOD OF PREPARING MONOESTERS

BACKGROUND OF THE INVENTION

The present application is a continuation-in-part of application Ser. No. 954,363, filed Oct. 25, 1978, abandoned.

FIELD OF THE INVENTION

The present invention relates generally to monoesters of dicarboxylic acids and monoesters of dihydric alcohols and, more particularly, to monoesterification of symmetrical dicarboxylic acids and diols with monohydric alcohols and monocarboxylic acids, respectively, to effect excellent yields (>90%, usually >95%).

Because monoesters of dicarboxylic acids or dihydric alcohols have both a reactive ester and acid or alcohol functionality, they are of value as intermediates in the synthesis of many types of useful chemicals. Such compounds are useful in the manufacture of fine organic chemicals, as starting materials for preparing ω-amino acids, in the synthesis of certain types of nylon, as precursors to macrocyclic ketones and lactones valued in perfumery, and as intermediates in the synthesis of insect pheromones. As one example, monoethyl sebacate prepared according to the present invention may be used as a starting material in the following synthesis of traumatic acid—a material useful both as a detergent additive (U.S. Pat. No. 3,523,636), and as an anti-viral agent (U.S. Pat. No. 3,542,826):

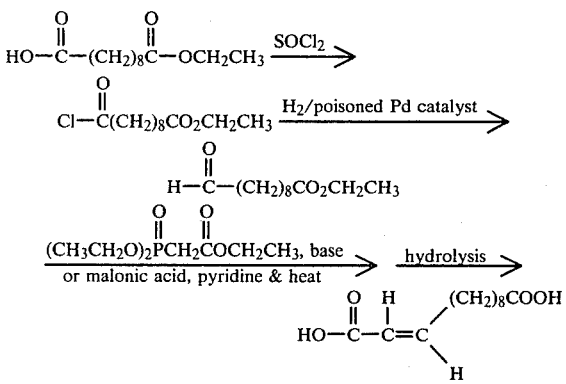

Monoesters of α, ω-diacids prepared in accordance with the present invention can also be utilized as starting materials in the preparation of nylon in a process suggested by C.S. Rondestvedt, Jr. [*J. Org. Chem.*, 42, 3118 (1977)]. Similarly, the monoacetate derivative of 1,8-octanediol can be used to prepare the attractant of the Oriental fruit moth:

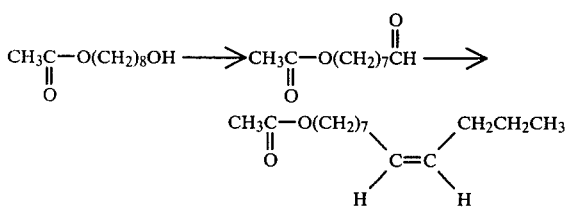

Description of the Prior Art

Although monoesters of dicarboxylic acids and dihydric alcohols are useful intermediates, a problem which has hindered prior art efforts to synthesize such compounds is the occurrence of esterification at both reactive sites. The result is the formation of a large quantity of diester as an undesired reaction product. These diesters are typically difficult to separate from the reaction mixture.

One prior art approach to the preparation of such monoesters has been to start with the unwanted diester and, via selective hydrolysis, to convert one ester function to an alcohol or acid function. For example:

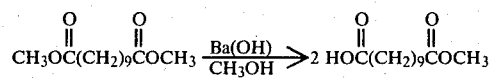

With the notable exception of the diester of terephthalic acid [Rondestvedt, *J. Org. Chem.*, 42, 3118 (1977)], this approach suffers from moderate yields (generally in the range of 40-70%) of the desired monoester, as well as some difficulty in separating the desired monoester from the reaction mixture, [i.e., *Organic Synthesis, Collective Vol.* 4, p. 635 (1963)].

Other approaches to the problem can be found in the literature, viz., *J. Am. Chem. Soc.*, 70, 364, 3206 (1948); *J. Org. Chem.*, 29, 1252 (1964); *Org. Syn. Coll. Vol.* 2, pp. 276-77 and references therein. All of these procedures present poor yields of the monoester and difficulty in eliminating the diester from the reaction product.

Of substantial interest to the background of the invention is the fact that the prior art uniformly suggests that esterification reactions should be run either under essentially anhydrous reaction conditions, or that the amount of water in the reaction be kept at a minimum. Indeed, since the process of ester formation from an acid and an alcohol is reversible, the reaction is generally performed under conditions providing for the water to be removed from the reaction mixture as soon as it is formed. This is necessary since water in the presence of a strong acid catalyst is known to effect the reverse process—i.e., hydrolysis of an ester.

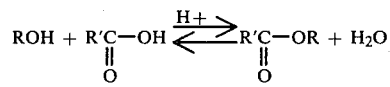

The prior art which does show that esterification can be achieved in the presence of water suggests both that the amount of water employed in the reaction mixture should be held at a minimum and that substantial amounts of diester will be formed even in such water-containing systems. Examples of such systems include U.S. Pat. No. 4,082,788 to Mims, German Pat. No. 2,404,359 to *Isoya et al.*, and German Pat. No. 2,015,709 to *BASF*.

BRIEF SUMMARY OF THE INVENTION

According to the present invention monesters of diacids and monoesters of diols are prepared in exceptionally high yields accompanied by the substantial reduction of diester products. The method of the invention, in contrast to the methods of the prior art, requires the presence of a substantial amount of water. Optimum results are obtained by employing as much water in the reaction mixture as is possible, consistent with the solubility of the reactants. The method can be illustrated by the following examples:

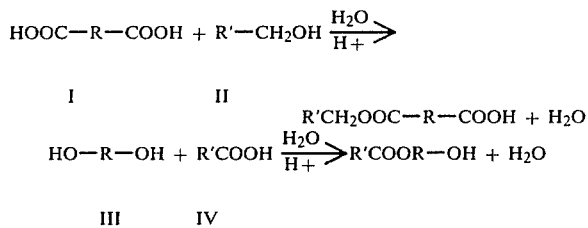

[wherein R is an alkyl group ($-CH_2-$)$_n$ and R' is an alkyl group or H.]

The method of the invention is applicable both to $C_2$ to $C_7$ diacids and diols having significant solubility in water (greater than 2g/100 ml) as well as to $C_8$ to $C_{12}$ diols and diacids which are only slightly soluble in water (less than 1g/100 ml). With respect to the $C_2$ to $C_7$ diacids and diols the amount of water utilized in the reaction mixture will always be present in high molar excess (>3 to 1 compared to the reactant monohydric alcohol or monocarboxylic acid).

With respect to the slightly soluble $C_8$ to $C_{12}$ diacids and diols, the virtual insolubility of these compounds at room temperature does not permit the use of large amounts of water. If one uses too much water with such slightly soluble materials, the monoesterification process of the present invention will proceed too slowly to be feasible. Nonetheless, it has been found that monoesters will be obtained in excellent yield as long as a molar excess of water (compared with the reactant monohydric alcohol or monocarboxylic acid) is employed. Failure to use a molar excess of water with such $C_8$ to $C_{12}$ materials will result in the formation of undesirable diester product.

Table I illustrates the solubility of some common diacids and diols as compiled from the *Handbook of Chemistry and Physics* and from R. T. Morrison and R. N. Boyd, *Organic Chemistry*, page 907 (2nd Ed.).

TABLE I

| Solubility in 100 g of water at 20° C. | |
| --- | --- |
| Oxalic acid | 9 grams |
| Malonic acid | 74 g |
| Succinic acid | 6 g |
| Glutaric acid | 64 g |
| Adipic acid | 2 g |
| Pimelic acid (heptanedioic acid) | 5 g |
| trans-1,4-cyclohexanedicarboxylic acid | <<1g |
| Suberic acid (octanedioic acid) | 0.2 g |
| Azelaic acid | 0.3 g |
| Sebacic acid | 0.1 g |
| Dodecanedioic acid | <<1g |
| Ethylene glycol | infinitely soluble |
| 1,3-Propanediol | infinitely soluble |
| 1,4-Butanediol | infinitely soluble |
| 1,5-Pentanediol | >3g |
| 1,6-Hexanediol | >3g |
| 1,4-Cyclohexanediol | >3g |
| 1,7-Heptanediol | >3g |
| 1,8-Octanediol | <<1g |
| 1,9-Nonanediol | <<1g |
| 1,10-Decanediol | <<1g |
| 1,12-Dodecanediol | <<1g |

Thus the exact amount of water employed will vary with the solubility of the diacid or diol in the water-alcohol or water-acid reagent mixture. However, it has been found that for a given diacid or diol, the more water used (consistent with solubility limits of the reactants), the better the results. Moreover, in all cases, the molar concentration of water should be greater than the molar concentration of the monohydric alcohol or monocarboxylic acid. With respect to the $C_2$ to $C_7$ diacids or diols even more water should be employed (greater than 75% on a molar basis). If less water is used, the desired monoesterification is virtually impossible to accomplish in even moderate yield.

In the case of both the diacid and diol starting materials, the reaction proceeds at room temperature. A strong acid catalyst ($Ka > 10^{-2}$) such as sulfuric acid greatly aids the reaction. In its absence, esterification can still occur—albeit quite slowly. The process of selective monoesterification depends upon the use of a technique of continuous extraction of the reaction mixture with a nonpolar solvent such as a liquid alkane, a cycloalkane, an aromatic hydrocarbon, a halide derivative of a hydrocarbon, or mixtures thereof. These nonpolar solvents are, of course, essentially insoluble in the aqueous reaction mixture. In a preferred method the solvent is heated to boiling, condensed, and the condensate passed through the aqueous reaction mixture by using, for example, a continuous extraction apparatus employing a reflux condenser.

Suitable solvents include hexane, heptane, cyclohexane, benzene, toluene, xylene, and carbon tetrachloride. Cyclohexane, in particular, works quite well. As a rule, starting material diols and diacids should be soluble in the aqueous reaction mixture yet virtually insoluble or of very low solubility in the nonpolar solvent used for the continuous extraction process. The resultant monoester product, however, is very soluble in the nonpolar solvent being passed through the reaction mixture. Thus, as soon as the less polar monoester product has formed, it is extracted out of the reaction mixture. The presence of a large amount of water (always >50% on a molar basis) permits this extraction to occur more readily and greatly retards the likelihood of diester formation.

A diacid or a diol suitable for use in the practice of the present invention must be symmetrical and have some appreciable solubility in a water-alcohol or water-acid mixture. Thus, while diacids and diols containing from 2 to 12 carbon atoms are particularly suitable, the process should also be useful for larger molecules having some degree of solubility in a water-alcohol or a water-acetic acid (for diols) mixture.

The symmetrical diols employed in processes according to the invention may be either primary or secondary acyclic or alicyclic compounds. Particularly useful compounds can be represented by formulae 1 through 3,

wherein: n has a value of from 0 to 10 inclusive

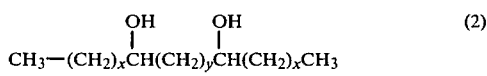

wherein: x has a value of from 0 to 4; y has a value of from 0 to 8; and $2x+y>8$

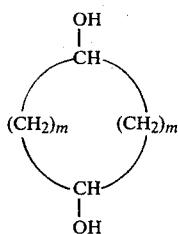

wherein m has a value of from 1 to 2.

The process fails for dihydric phenols such as resorcinol (4).

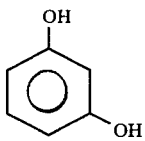

Symmetrical diacids useful in practice of the invention include acyclic diacids of the general structural formula, 5, wherein R represents a chemical bond or a straight chain alkylene having up to ten carbons, and the cyclic diacid, 1,4-cyclohexanedicarboxylic acid, of formula 6. The process is unsuccessful both with terephthalic acid, 7, since it is insoluble in water-alcohol, and with phthalic acid, 8, since it readily forms the corresponding anhydride, 9.

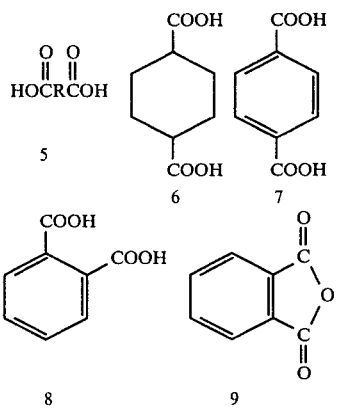

Monohydric alcohols useful in the esterification of diacids according to the invention include both methanol and ethanol. It has been found that higher molecular weight, water-soluble alcohols, such as n-propanol and isopropanol, are unsatisfactory. Despite their solubility in water, such higher monohydric alcohols tend to be soluble in the nonpolar organic solvent used in the continuous extraction process. Moreover, when the nonpolar solvent "picks up" the higher alcohol, this mixture very quickly extracts over the starting diacid making it virtually impossible to carry out the esterification reaction in the aqueous layer. More significantly, the reaction vessel containing the refluxing nonpolar organic solvent will, when higher monohydric alcohols are employed, build up an appreciable concentration of the alcohol and an esterification reaction can occur in the organic solvent mixture, leading to the formation of the undesired diester.

Similar problems arise upon attempted use of propionic or higher water-soluble acids to monoesterify diols. These higher acids are sufficiently soluble in the nonpolar solvent to prevent their use in the continuous esterification process. Thus the only monocarboxylic acids useful for the monoesterification of diols are alkanoic acids having up to two carbon atoms. Of this group, acetic acid is the preferred monocarboxylic acid, although formic acid can be used—if the selected diol is soluble in an aqueous formic acid mixture.

The procedure employed to isolate the desired monoester from the starting reactants can vary depending on the nature of the starting diacid or diol. Gas chromatographic analysis ("GC") of the products derived from reaction involving low molecular weight, non-crystalline diols such as ethylene glycol did not indicate the presence of any starting diol. Thus no further isolation is necessary, save removal of the nonpolar solvent by distillation.

The C-2 through C-12 diacids, as well as the C-6 through C-12 diols, are all highly crystalline and virtually insoluble in the nonpolar solvent used for the continuous extraction process. As soon as the extraction solvent is allowed to cool to room temperature, the diacid (or diol) that has been extracted over (if any at all) by the nonpolar organic solvent can be removed by simple filtration and may be re-cycled. As the number of carbons in the diacid or diol becomes larger (i.e., 10 or more carbons), this process of re-cycling the starting material becomes more desirable.

After removal of any starting diacid or diol by filtration, the nonpolar solvent can be removed by distillation (under reduced pressure, if one so desires) and the purity of monoester so obtained is >95% in most systems examined. If one desires even higher purity, recrystallization of the monoesters from a suitable solvent may be easily performed since many of the monoesters are solids at room temperature. Alternatively, in the case of diacid derived products, the monoester is still acidic and can be separated from any diester by extraction into an aqueous phase using a weak base such as sodium bicarbonate. Subsequent acidification of the aqueous layer containing the acid salt allows recovery of the desired monoester.

DETAILED DESCRIPTION

The following examples illustrate in greater detail practice of the present invention.

EXAMPLE I 1,10-decanediol monoacetate

A solution of 4.36 g (25 mmoles) of 1,10-decanediol in 100 ml (1.77 moles) of glacial acetic acid was mixed with 130 ml (7.22 moles) of $H_2O$ containing 0.25 ml (4.5 mmoles) of conc. $H_2SO_4$. This mixture, itself at room temperature, was then extracted continuously for two days using refluxing cyclohexane. The cyclohexane layer was then cooled to room temperature and 0.78 g (18% recovery) of crystalline 1,10-decanediol was recovered by simple filtration of this nonpolar organic phase. The cyclohexane was then removed from the filtrate under reduced pressure, affording 4.28 g (approximately 79% yield—97% based on recovered starting material of product. GC analysis showed the presence of less than 2% starting diol; the ratio of monoester to diester was 20 to 1. Hence the desired monoester was approximately 95% pure.

EXAMPLE II

In a procedure similar to that of Example I, a solution of 4.25 g (24.4 mmoles) of 1,10-decanediol and 0.25 ml of conc. $H_2SO_4$ in 200 ml (3.53 moles) of glacial acetic acid and 30 ml (1.66 moles) of $H_2O$ was extracted continuously with cyclohexane for 20 hours. The cyclohexane layer was then cooled to room temperature and the solvent was removed under reduced pressure using a rotary evaporator leaving behind 5.52 g of crude product. GC analysis indicated the presence of 3% diol, 41% monoester, and 56% of the diester—1,10-decanediol diacetate. Since this procedure used only ~33% $H_2O$ (on a molar basis), the need for water (to minimize formation of the undesirable diester) is established. In the previous Example I, the aqueous layer was ~80% $H_2O$ and ~20% acetic acid on a molar basis.

EXAMPLE III

Monoethyl sebacate

A solution of 3.093 g (15.3 mmoles) of sebacic acid in 100 ml (1.63 moles) of 95% ethanol was mixed with 120 ml of $H_2O$ (6.94 moles $H_2O$, total) containing 1 ml (18 mmoles) of conc. $H_2SO_4$. [This aqueous solution is approximately 81% $H_2O$ and 19% ethyl alcohol on a molar basis.] This solution was extracted continuously for two days using refluxing cyclohexane. The cyclohexane layer was then cooled to room temperature and 0.74 g (24% recovery) of sebacic acid was recovered by simple filtration of this nonpolar organic phase. After filtering off the sebacic acid, the cyclohexane layer was washed 15 times with 1 M aqueous $NaHCO_3$ solution (15×10 ml) in order to effect separation of monoethyl sebacate from any diethyl sebacate, which remained in the organic layer. Each of these sodium bicarbonate washes was added to an Erlenmeyer flask containing 100 ml of ice-cold 2 M aqueous HCl solution. The cyclohexane layer was then dried over anhydrous magnesium sulfate and filtered. Removal of the cyclohexane by evaporation at reduced pressure afforded 103 mg (0.40 mmole, 2.6% yield) of diethyl sebacate. The monoester was recovered from the aqueous hydrochloric acid mixture by thorough extraction with ethyl ether. The combined extracts were washed with 10% sodium chloride solution, dried over anhydrous magnesium sulfate, and filtered. Removal of the ether by evaporation at reduced pressure yielded 2.25 g (9.78 mmoles, 64% yield) of monoethyl sebacate. The ratio of monoester to diester in this procedure was therefore 64 to 2.6 or approximately 25 to 1. Since the purity of monoethyl sebacate without separating it from any diester is >96%, there appeared to be no substantial need for the sodium bicarbonate washes and the rest of the workup procedures.

EXAMPLE IV

A procedure similar to that of Example III was carried out by mixing a solution of 3.09 g (15.3 mmoles) of sebacic acid in 150 ml (2.44 moles) of 95% ethanol with 20 ml of $H_2O$ (1.53 moles $H_2O$, total) containing 0.75 ml (13.5 mmoles) of conc. $H_2SO_4$. This solution was then extracted continuously with refluxing cyclohexane for 27 hours. The reaction products were isolated as described in Example III. Results: 617 mg (20% recovery) of sebacic acid which can be re-cycled in this monoesterification process; 753 mg (2.92 mmoles, 19% yield) of diethyl sebacate; and 1.72 g (7.48 mmoles, 49% yield) of monoethyl sebacate. The ratio of monoester to diester in this procedure was therefore 49 to 19 or approximately 2½ to 1. It is noteworthy that the aqueous solution in this procedure was approximately 38% water on a molar basis and the concentration of $H_2SO_4$ was approximately 0.08 M. In example III, the concentration of sulfuric acid was approximately 0.08 M and the aqueous solution was 81% water on a molar basis.

EXAMPLE V

Monoethyl adipate

A solution of 4.00 g (27.4 mmoles) of adipic acid in 30 ml of absolute ethanol (514 mmoles) was mixed with 180 ml (10 moles) of water containing 4 ml (72 mmoles) of conc. $H_2SO_4$. This solution was then extracted continuously for five days using benzene. The benzene layer was then cooled to room temperature and trace amounts of crystalline adipic acid were removed by filtration prior to isolation of the reaction products. After filtration, the benzene layer was washed thoroughly with 1 M aqueous sodium bicarbonate solution, each wash being added to a flask containing sufficient aqueous hydrochloric acid to neutralize all of the $NaHCO_3$, in order to liberate monoethyl adipate from its salt. Dilute aqueous $Na_2CO_3$ solution, but not dilute aqueous NaOH, can be used in lieu of the sodium bicarbonate solution. If one uses aqueous sodium hydroxide to effect conversion of monoethyl adipate to a water-soluble salt, a substantial amount of hydrolysis of the monoester occurs while it is dissolved in the the aqueous NaOH solution. The benzene layer (containing diethyl adipate) was then dried over anhydrous magnesium sulfate and filtered. Removal of the benzene by evaporation at reduced pressure afforded 206 mg (1.02 mmoles, 3.7% yield) of diethyl adipate: bp (bath temperature) 55°–65° at 0.2 mm. The monoester was recovered from the aqueous hydrochloric acid mixture by thorough extraction with ethyl ether. The combined extracts were washed with 10% sodium chloride solution, dried over anhydrous magnesium sulfate, and filtered. Removal of the ether by evaporation at reduced pressure yielded 4.16 g (87.5% yield) of monoethyl adipate as a low melting solid, mp (after one recrystallization from ether-pentane): 28°–30° C.

Since the ratio of monoester to diester was approximately 96:4, there seems to be no substantial need for the sodium bicarbonate washes for the purification of the monoester via formation of a water-soluble carboxylate salt. Simple removal of the benzene should yield a product that is 96% pure. If greater purity is desired, the monoester can be recrystallized.

EXAMPLE VI

Monoethyl dodecanedioate

A solution of 4.616 g (20.1 mmoles) of dodecanedioic acid in 150 ml (2.44 moles) of 95% ethanol was mixed with 80 ml (4.44 moles) of $H_2O$ containing 1 ml (18 mmoles) of conc. $H_2SO_4$. The mixture was not homogeneous at this point; as much as 50% of the starting diacid precipitated out of solution when the water was added to the ethanol containing this C-12 diacid. As the reaction proceeded, however, the diacid slowly re-dissolved in the aqueous layer and the reaction was able to be completed within the normal period of time.

This mixture was extracted continuously for 2½ days using cyclohexane. The cyclohexane layer was then cooled to room temperature and 1.40 g (30% recovery)

of dodecanedioic acid was recovered by simple filtration of this nonpolar organic phase. After filtering off this solid diacid, the monoester was separated from any diester in the cyclohexane layer by thorough extraction with 1 M aqueous NaHCO$_3$ solution. The exact procedure followed has previously been described in Example III. Results: The yield of diethyl dodecanedioate was only 63 mg (0.22 mmole, 1% yield); the recovery of monoethyl dodecanedioate was 3.58 g (13.9 mmoles, 69% yield). The mp of this monoester (after recrystallization from ethanol-H$_2$O) was 37°–38° C. Since the ratio of monoester to diester was 69:1, there is no need for the lengthy workup procedure involving NaHCO$_3$. After filtering off any recovered starting diacid, the cyclohexane can be removed by evaporation under reduced pressure and the monoester should at that point be >98% pure. In a separate procedure, only 2 g of dodecanedioic acid was used and the rest of the reagents were kept the same. In this latter procedure, the aqueous layer remained homogeneous but the final results (product ratios, etc.) were the same as the first procedure. Hence it is not necessary that the diacid be totally dissolved in the aqueous layer.

EXAMPLE VII

1,8-octanediol monoacetate

A solution of 1.987 g (13.7 mmoles) of 1,8-octanediol in 25 ml (441 mmoles) of glacial acetic acid was mixed with 200 ml (11.11 moles) of H$_2$O containing 4 ml (72 mmoles) of conc. H$_2$SO$_4$. This mixture was extracted continuously for 40 hours using hexane. The monoester is not very soluble in hexane and hence a mixture of hexane-cyclohexane (in which the monoester, but not the starting diol, is soluble) should be recommended if one is interested in developing this process for 1,8-octanediol. After cooling the hexane to room temperature, ether was added to make the organic layer homogeneous. The ether-hexane layer was then dried over anhydrous potassium carbonate and filtered. Removal of the solvent under reduced pressure afforded 2.38 g (~92% yield) of product, GC analysis of which indicated the presence of 2% starting diol and 4% diester. The purity of the desired monoester was therefore 94%.

EXAMPLE VIII

When selected diacids and diols are reacted with aqueous solutions of a monohydric alcohol or a monocarboxylic acid in the presence of a strong acid catalyst, monoesters can be isolated as illustrated in Table II.

TABLE II

| Reagent | Aqueous Reagent Mixture | Catalyst | Time | Solvent Used for Extraction | % Recovery of Starting Material | Ratio of Monoester to Diester |
|---|---|---|---|---|---|---|
| 61.5 mmoles of oxalic acid dihydrate | 80 ml of 95% ethanol and 160 ml of H$_2$O | 1 ml conc. H$_2$SO$_4$ | 3 days | benzene | 4% | 90:1 |
| 29 mmoles of 1,4-cyclohexanedicarboxylic acid | 100 ml of CH$_3$OH and 200 ml of H$_2$O | 1 ml conc. H$_2$SO$_4$ | 24 hours | benzene | <5% | 92:1 |
| 15 mmoles of 1,10-decanediol | 75 ml of glacial acetic acid and 155 ml of H$_2$O | 0.25 ml conc. H$_2$SO$_4$ | 1½ days | 5:1 (v/v) cyclohexane: CCl$_4$ | 35% (which can be re-cycled) | 60:1 |
| 7 mmoles of 1,12-dodecanediol | 150 ml of glacial acetic acid and 90 ml of H$_2$O | 0.25 ml conc. H$_2$SO$_4$ | 30 hours | cyclohexane | 25% (re-cyclable) | 66:5 |
| 36 mmoles of ethylene glycol | 80 ml of glacial acetic acid and 160 ml of H$_2$O | 0.50 ml conc. H$_2$SO$_4$ | 1 week | benzene | None | 94:6 |
| 17 mmoles of 1,4-cyclohexanediol | 45 ml of glacial acetic acid and 180 ml of H$_2$O | 4.0 ml conc. H$_2$SO$_4$ | 4 days | benzene | 14%* (can be precipitated out) | 85:1 |
| 17 mmoles of 1,4-cyclohexanediol | 60 ml of glacial acetic acid and 180 ml of H$_2$O | 4.0 ml conc. H$_2$SO$_4$ | 4 days | 2:1 (v/v) cyclohexane: benzene | 2% | 90:8 |
| 15 mmoles of 1,10-decanediol | 90 ml of glacial acetic acid and 120 ml of H$_2$O | 0.25 ml conc. H$_2$SO$_4$ | 1½ days | 1:1 (v/v) hexane: cyclohexane | 22% (Re-cyclable) | 75:3 |
| 15 mmoles of 1,10-decanediol | 100 ml of glacial acetic acid and 130 ml of H$_2$O | None | 3 days | cyclohexane | 56% | >40:1 |

*Can be precipitated out of the benzene layer by the addition of hexane.

What is claimed is:

1. A method of preparing a monoester which comprises:
    preparing a reaction mixture selected from the group consisting of
    (a) an alkanoic acid selected from the group consisting of formic and acetic, an acid catalyst, water in an amount whereby the ratio of the molar concentration of water to alkanoic acid is greater than 3 to 1, and a symmetrical diol soluble in the alkanoic acid-water mixture, said diol selected from those of the forulae HOCH$_2$(CH$_2$)$_n$CH$_2$OH wherein n has a value from 0 to 5, inclusive,

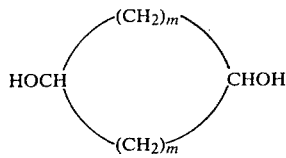

wherein m has a value of 1 or 2,

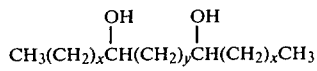

wherein x has a value of 0 or 1, y has a value of from 0 to 3, and $(2x+y)<4$;
(b) an alcohol selected from the group consisting of methanol and ethanol, an acid catalyst, water in an amount whereby the ratio of the molar concentration of water to alcohol is at least 3 to 1, and a symmetrical dicarboxylic acid soluble in the alcohol-water mixture, said acid selected from the group consisting of diacids of the formula

wherein R represents a chemical bond or a straight chain alkylene having up to 5 carbons;
continuously extracting the reaction mixture with a nonpolar solvent which is essentially insoluble in the reaction mixture and in which the reactants have no more than slight solubility, to form a monoester of the reactants of (a) or (b), soluble in the nonpolar solvent,
separating the nonpolar solvent containing the monoester from the reaction mixture, and
isolating the monoester from the nonpolar solvent.

2. A method of preparing a monoester which comprises:
preparing a reaction mixture selected from the group consisting of
(a) an alkanoic acid selected from the group consisting of formic and acetic, an acid catalyst, an amount of water greater than the molar concentration of the alkanoic acid, and a symmetrical diol soluble in the alkanoic acid-water mixture, said diol selected from those of the formulae

$HOCH_2(CH_2)_nCH_2OH$ wherein n has a value of 6 to 10, inclusive,

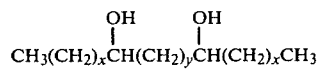

wherein x has a value of from 0 to 4, y has a value of from 0 to 8, and $4<(2x+y)<8$;
(b) an alcohol selected from the group consisting of methanol and ethanol, an acid catalyst, an amount of water greater than the molar concentration of the alcohol, and a symmetrical dicarboxylic acid soluble in the alcohol-water mixture, said acid selected from the group consisting of 1,4-cyclohexanedicarboxylic acid and diacids of the formula

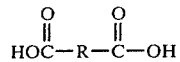

wherein R represents a straight chain alkylene having between 6 and 10 carbons;
continuously extracting the reaction mixture with a nonpolar solvent which is essentially insoluble in the reaction mixture and in which the reactants have no more than slight solubility, to form a monoester of the reactants of (a) or (b), soluble in the nonpolar solvent,
separating the nonpolar solvent containing the monoester from the reaction mixture, and
isolating the monoester from the nonpolar solvent.

3. The improvement of claim 1 wherein said nonpolar solvent is an alkane, a cycloalkane, an aromatic hydrocarbon, or a halide derivative of hydrocarbon.

4. The improvement of claim 2 wherein said nonpolar solvent is an alkane, a cycloalkane, an aromatic hydrocarbon, or a halide derivative of hydrocarbon.

5. A method for synthesis of monoesters of symmetrical diols, said method comprising:
(a) forming an ester-forming reaction mixture of
(i) a symmetrical diol selected from among those of the formulae $HOCH_2(CH_2)_nCH_2OH$ wherein n has a value of 6 to 10, inclusive,

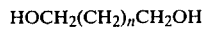
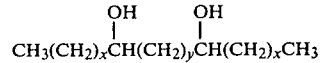

wherein x has a value of from 0 to 4, y has a value of from 0 to 8, and $4\leq(2x+y)\leq 8$;
(ii) a monocarboxylic acid selected from the group consisting of acetic acid and formic acid,
(iii) water in an amount at least greater than the concentration of the monocarboxylic acid, and
(iv) a strong acid catalyst;
(b) continuously extracting said reaction mixture with a nonpolar solvent; and
(c) isolating a monoester from said nonpolar solvent.

6. A method for synthesis of monoesters of symmetrical diols, said method comprising:
(a) forming an ester-forming reaction mixture of
(i) a symmetrical diol selected from among those of the formulae $HOCH_2(CH_2)_nCH_2OH$ wherein n has a value of from 0 to 5, inclusive,

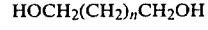
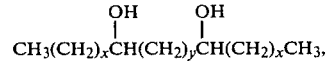

wherein x has a value of 0 or 1, y has a value from 0 to 3, and $2x+y$ is less than 4;

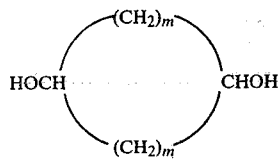

wherein m has a value of from 1 to 2;

(ii) a monocarboxylic acid selected from the group consisting of acetic acid and formic acid, (iii) water in an amount whereby the ratio of the molar concentration of water to monocarboxylic acid is at least 3 to 1, and (iv) a strong acid catalyst;

(b) continuously extracting said reaction mixture with a nonpolar solvent; and (c) isolating a monoester from said nonpolar solvent.

7. A method for synthesis of monoesters of symmetrical dicarboxylic acids, said method comprising:

(a) forming a reaction mixture of (i) a symmetrical dicarboxylic acid selected from among diacids of the formula

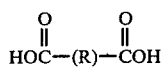

wherein R represents a chemical bond or a straight chain alkylene having up to 5 carbons, (ii) a monohydric alcohol selected from the group consisting of ethanol and methanol (iii) water in an amount whereby the ratio of the molar concentration of water to monohydric alcohol is at least 3 to 1; and (iv) a strong acid catalyst;

(b) continuously extracting said reaction mixture with a nonpolar solvent;

(c) isolating a monoester from said nonpolar solvent.

8. A method for synthesis of monoesters of symmetrical dicarboxylic acids, said method comprising:

(a) forming a reaction mixture of (i) a symmetrical dicarboxylic acid selected from among the group 1,4-cyclohexanedicarboxylic acid and diacids of the formula

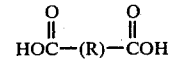

wherein R represents a straight chain alkylene having between 6 and 10 carbons;

(ii) a monohydric alcohol selected from the group consisting of ethanol and methanol, (iii) water in an amount greater than the concentration of the monohydric alcohol; and (iv) a strong acid catalyst;

(b) continuously extracting said reaction mixture with a nonpolar solvent; and (c) isolating a monoester from said nonpolar solvent.

9. The improvement of claim 8 further including the step of recovering said symmetrical dicarboxylic acid from said nonpolar solvent.

10. The improvement of claim 5 further including the step of recovering said symmetrical diol from said nonpolar solvent.

* * * * *

UNITED STATES PATENT AND TRADEMARK OFFICE
CERTIFICATE OF CORRECTION

PATENT NO. : 4,314,071
DATED : February 2, 1982
INVENTOR(S) : James H. Babler

It is certified that error appears in the above-identified patent and that said Letters Patent are hereby corrected as shown below:

Column 4, line 68, " $2x+y > 8$ " read -- $2\underline{x} + \underline{y} \leq 8$ --.

Column 8, line 5 change "In example" to --In Example--

Column 8, line 25 change "solution, but not" to
--solution, but <u>not</u>--

Column 11, line 61 " $4 < (2x+y) \leq 8$ ;" read -- $4 \leq (2\underline{x} + \underline{y}) \leq 8$; --.

Signed and Sealed this

Twentieth Day of July 1982

[SEAL]

Attest:

Attesting Officer

GERALD J. MOSSINGHOFF

*Commissioner of Patents and Trademarks*